United States Patent [19]

Murata et al.

[11] 4,247,480
[45] Jan. 27, 1981

[54] PROCESS FOR PRODUCING AMINEOXIDE

[75] Inventors: Atsuo Murata; Syuji Tsuchiya; Akihiro Konno; Fumiyoshi Arima; Hisao Ikeda, all of Funabashi, Japan

[73] Assignee: Nissan Chemical Industries Limited, Tokyo, Japan

[21] Appl. No.: 65,338

[22] Filed: Aug. 9, 1979

[30] Foreign Application Priority Data

Aug. 24, 1978 [JP] Japan ............................. 53-103231

[51] Int. Cl.³ .......................................... C07C 135/02
[52] U.S. Cl. .................................................. 564/298
[58] Field of Search ................................... 260/583 D

[56] References Cited

U.S. PATENT DOCUMENTS

| | | | |
|---|---|---|---|
| 3,283,007 | 11/1966 | Chadwick | 260/583 D |
| 3,333,000 | 7/1967 | Albert et al. | 260/583 D |
| 3,432,555 | 3/1969 | Mahnken | 260/583 D |
| 3,463,817 | 8/1969 | Mahnken | 260/583 D |

FOREIGN PATENT DOCUMENTS

| | | | |
|---|---|---|---|
| 2448641 | 4/1975 | Fed. Rep. of Germany | 260/583 D |
| 2557456 | 6/1976 | Fed. Rep. of Germany | 260/583 D |
| 51-32505 | 3/1976 | Japan | 260/583 D |

OTHER PUBLICATIONS

Basov et al., "Chem. Ab.", vol. 78, Ab. no. 124003h (1973).

*Primary Examiner*—John Doll
*Attorney, Agent, or Firm*—Oblon, Fisher, Spivak, McClelland & Maier

[57] ABSTRACT

An amine oxide is produced by oxidizing a tertiary amine having the formula

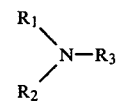

wherein $R_1$ and $R_2$ respectively represent methyl or ethyl group; and $R_3$ represent a $C_8$–$C_{14}$ alkyl or alkenyl group in the presence of carbon dioxide and in the presence or absence of an improver selected from the group consisting of ethylenediaminetetraacetic acid, its salts, stanates, polyphosphates, salts of hydroxycaboxylic acid and salts of polycarboxylic acid.

10 Claims, No Drawings

PROCESS FOR PRODUCING AMINEOXIDE

BACKGROUND OF THE INVENTION

1. Field of the Invention

The present invention relates to an improved process for producing a tertiary amineoxide. More particularly, it relates to a process for producing a tertiary amineoxide by oxidizing a tertiary amine with hydrogen peroxide.

2. Description of the Prior Arts

It has been known that an amineoxide is produced by oxidizing a tertiary amine with hydrogen peroxide in the presence of a chelating agent.

The process for producing a tertiary amineoxide by oxidizing a tertiary amine with hydrogen peroxide in the presence of a chelating agent of diethylenetriamine pentaacetic acid or it salt has been disclosed in Japanese Examined Patent Publication No. 14089/1976 wherein 30-75% aqueous solution of hydrogen peroxide has been added to the tertiary amine at 55 to 65° C. at a ratio of excess of about 10% and the reaction has been completed at 65° to 80° C.

The process for producing a tertiary amineoxide by oxidizing a tertiary amine with hydrogen peroxide in the presence of sodium pyrophosphate and sodium bicarbonate has been disclosed in Japanese Examined Patent Publication 11042/1967.

The inventors have studied on the process for producing an amineoxide by oxidizing a tertiary amine with hydrogen peroxide.

SUMMARY OF THE INVENTION

It is an object of the present invention to provide an improved process for producing an amineoxide by oxidizing a tertiary amine with hydrogen peroxide at high and constant yield for a short time.

The foregoing and other objects of the present invention have been attained by oxidizing a tertiary amine with hydrogen peroxide in the presence 0.01-2% by weight based on the amine of carbon dioxide ($CO_2$) in the presence or the absence of an improver selected from the group consisting of ethylenediaminetetraacetic acid and its salts; stanates polyphosphates; salts of hydroxycarboxylic acid and salts of polycarboxylic acid.

DETAILED DESCRIPTION OF THE PREFERRED EMBODIMENTS

In accordance with the process of the present invention, the amount of the tertiary amine can be decreased to less than 0.5%. The characteristic feature of the present invention is to obtain the tertiary amineoxide at substantially constant yield for a short time by reacting a tertiary amine with hydrogen peroxide in carbon dioxide even though a chelating agent is not used because the effect of carbon dioxide is remarkably high. Such fact has not been considered.

When a glass reactor is used, it is enough to use only carbon dioxide. However, when a metallic reactor is used, hydrogen peroxide may be decomposed to cause an incomplete reaction. In such case, the reaction can be smoothly performed to cause a complete reaction by incorporating carbon dioxide and a chelating additive.

When the reaction is repeated, the reaction can be performed without the chelating additive by incorporating carbon dioxide even in a metallic reactor.

In accordance with the process of the present invention, an amineoxide can be obtained at high yield without using an expensive catalyst. The safety is improved over the conventional process by incorporating carbon dioxide.

The reaction of the present invention can be attained without using an organic solvent if desired.

Hydrogen peroxide is preferably used as 5 to 70 wt.% of a hydrogen peroxide aqueous solution.

When the concentration of hydrogen peroxide is less than 5%, a self decomposition of hydrogen peroxide is caused to prevent the complete oxidation except that a large excess of the specific additive should be used.

Hydrogen peroxide can be used at a concentration of greater than 70%. However, the yield of the amineoxide is decreased and the feature is not preferable in view of the safety and the operation.

An amount of hydrogen peroxide can be the stoichometric amount and it is preferable to be excess of 5 to 10% to the stoichometric amount especially when the conversion of the tertiary amine of more than 99% is required.

In the oxidation, the improver is incorporated.

Suitable improvers include ethylenediaminetetraacetic acid and its salts, stanate such as sodium stanate; polyphosphates such as sodium pyrophosphate and tripolyphosphate; salts of hydroxycarboxylic acid such as sodium citrate; salts of polycarboxylic acid such as sodium oxalic acid.

An amount of the improver is ranging from 0.02 to 2 wt.% preferably from 0.05 to 1 wt.% to the amine.

An amount of carbon dioxide is ranging from 0.01 to 2 wt.% preferably 0.03 to 1 wt.% to the amine.

When carbon dioxide is not incorporated in the reaction system, a decomposition of hydrogen peroxide is caused whereby a large amount of the unreacted amine is remained and a reaction velocity is low. It is considered that carbon dioxide has certain catalytic effect in the oxidation.

The method of the incorporation of carbon dioxide is not critical. Thus, it is preferable to add hydrogen peroxide to the amine in which carbon dioxide and the improver are incorporated.

The reaction temperature is ranging from 40° to 80° C.

The amines used in the process of the present invention are aliphatic tertiary amines having the formula

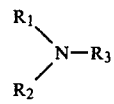

wherein $R_1$ and $R_2$ respectively represent methyl or ethyl group; $R_3$ represents a $C_8$-$C_{14}$ alkyl or alkenyl group.

The typical amines used for the process of the present invention include N,N-dimethyl 3,7-dimethyl 2-6-octadienylamine and N,N-diethyl 3,7-dimethyl 2-6-octadienylamine.

The present invention will be further illustrated by certain examples and references which are provided for purposes of illustration only and are not intended to be limiting the present invention.

EXAMPLE 1

In a 300 ml. four necked flask equipped with a stirrer and a thermometer, 83.6 g. (0.4 mole) of N,N-diethyl 3,7-dimethyl 2-6-octadienylamine and sodium stanate (400 ppm based on the amine) and carbon dioxide (2000 ppm based on the amine) were charged. The mixture was stirred at 55° C. and 49.8 g. of 30% hydrogen peroxide (1.1 mole based on the amine) was added dropwise to the mixture. After the addition, the reaction was continued at 65° C. for 4 hours. As a result, N,N-diethyl 3,7-dimethyl 2-6-octadienylamineoxide was obtained at the yield of 99.0% to remain 1.0% of the unreacted amine.

EXAMPLE 2

In a 5 liter four necked round bottom flask, 1672 g. (8 mole) of N,N-diethyl 3,7-dimethyl 2-6-octadienylamine was charged and carbon dioxide was introduced into the reactor to purge air (0.4 wt.% of carbon dioxide to the amine). The amine was stirred at 60° to 65° C. and 95.2 g. of 30% hydrogen peroxide (1.05 mole based on the amine) added dropwise to the amine during 2 hours.

After the addition of the hydrogen peroxide, the reaction was continued for 2 hours. As a result, N,N-diethyl 3,7-dimethyl 2-6-octadienylamineoxide was obtained at the yield of 99.2% to reamin 0.8% of the unreacted amine.

EXAMPLES 3 to 8

In accordance with the process of Example 1 except varying the improver carbon dioxide, the reaction temperature and the reaction time as shown in Table 1, each reaction was carried out. The results are shown in Table 1.

TABLE 1

|  | Ref. 1 | Ref. 2 | Exp. 3 | Exp. 4 |
|---|---|---|---|---|
| Amount of $H_2O_2$ (g) | 35%<br>42.7 | 30%<br>49.8 | 30%<br>49.8 | 30%<br>49.8 |
| Amount of N,N-diethyl 3,7-dimethyl 2-6-octadienylamine (g) | 83.6 | 83.6 | 83.6 | 83.6 |
| Additive | none | EDTA-2Na<br>0.1 wt. % | none | $Na_4P_2O_7$<br>0.2 wt. % |
| $CO_2$ gas | none | none | $CO_2$<br>0.2 wt. % | $CO_2$<br>0.2 wt. % |
| Reaction temp. (°C.) | 65 | 65 | 65 | 65 |
| Reaction time (hr.) | 8 | 8 | 4 | 4 |
| Yield of amineoxide (%) | 73.1 | 90.6 | 98.8 | 98.5 |
| Unreacted amine (%) | 21.4 | 7.1 | 0.1 | 0.4 |

TABLE 1'

|  | Exp. 5 | Exp. 6 | Exp. 7 | Exp. 8 |
|---|---|---|---|---|
| Amount of $H_2O_2$ (g) | 20%<br>74.8 | 50%<br>29.9 | 30%<br>49.8 | 30%<br>49.8 |
| Amount of N,N-diethyl 3,7-dimethyl 2-6-octadienylamine (g) | 83.6 | 83.6 | 83.6 | 83.6 |
| Additive | $Na_4P_2O_7$ | $Na_4P_2O_7$ | EDTA-4Na | $Na_5P_3O_{10}$ |
| $CO_2$ gas | 0.2 wt. %<br>$CO_2$<br>0.2 wt. % | 0.2 wt. %<br>$CO_2$<br>0.2 wt. % | 0.1 wt. %<br>$CO_2$<br>0.4 wt. % | 0.2 wt. %<br>$CO_2$<br>0.4 wt. % |
| Reaction temp. (°C.) | 65 | 65 | 65 | 65 |
| Reaction time (hr.) | 4 | 4 | 4 | 4 |
| Yield of amineoxide (%) | 98.7 | 96.0 | 97.5 | 98.4 |
| Unreacted amine (%) | 0.1 | 2.8 | 1.5 | 0.7 |

We claim:

1. A process for producing an amineoxide which comprises oxidizing a tertiary amine having the formula

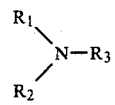

wherein $R_1$ and $R_2$ respectively represent methyl or ethyl group; $R_3$ represents a $C_8$–$C_{14}$ alkyl or alkenyl group in the presence of carbon dioxide, with hydrogen peroxide;
wherein 0.01 to 2 weight % of carbon dioxide based on the tertiary amine is incorporated in the reaction system.

2. A process for producing an amineoxide according to claim 1 wherein the oxidization is carried out in the presence of an improver selected from the group consisting of ethylenediaminetetraacetic acid, its salts, stanates, polyphosphates, salts of hydroxycarboxylic acid and salts of polycarboxylic acid.

3. A process for producing an amineoxide according to claim 2 wherein 0.02 to 2 wt.% of the improver based on the tertiary amine is incorporated in the reaction system.

4. A process for producing an amineoxide according to claim 1 wherein the tertiary amine is N,N-diethyl 3,7-dimethyl 2-6-octadienylamine or N,N-dimethyl 3,7-dimethyl 2-6-octadienylamine.

5. The process of claim 1, wherein the reaction is carried out in a glass reactor.

6. The process of any of claims 1 or 2, wherein the reaction is carried out in a metal reactor.

7. The process of claim 1, wherein the hydrogen peroxide is a 5–70% by weight aqueous solution.

8. The process of claim 1, wherein 5–10% of a stoichiometric excess of hydrogen peroxide over amine is used.

9. The process of claim 1, wherein the amount of said carbon dioxide is 0.03–1 weight % based on the tertiary amine.

10. The process of claim 1, wherein the reaction temperature is about 40°–80° C.

* * * * *